(12) United States Patent
Nadkarni et al.

(10) Patent No.: US 7,939,102 B2
(45) Date of Patent: May 10, 2011

(54) CONTROLLED RELEASE FORMULATION OF LAMOTRIGINE

(75) Inventors: Sunil Sadanand Nadkarni, Gujarat (IN); Navin Vaya, Gujarat (IN)

(73) Assignees: Torrent Pharmaceuticals Ltd., Ahmedabad (IN); Torrent Pharmaceuticals Torrent Research Center, Gujarat (IN)

( * ) Notice: Subject to any disclaimer, the term of this patent is extended or adjusted under 35 U.S.C. 154(b) by 379 days.

(21) Appl. No.: 10/452,772

(22) Filed: Jun. 2, 2003

(65) Prior Publication Data

US 2004/0043996 A1    Mar. 4, 2004

(51) Int. Cl.
*A61K 9/26* (2006.01)
(52) U.S. Cl. ........................................... 424/470
(58) Field of Classification Search .............. None
See application file for complete search history.

(56) References Cited

U.S. PATENT DOCUMENTS

| | | | |
|---|---|---|---|
| 5,326,570 | A | 7/1994 | Rudnic et al. |
| 5,536,507 | A | 7/1996 | Abramowitz et al. |
| 5,556,639 | A | 9/1996 | Fielden |
| 5,637,320 | A | 6/1997 | Bourke et al. |
| 5,863,558 | A * | 1/1999 | Jao et al. ............... 424/465 |
| 6,194,000 | B1 * | 2/2001 | Smith et al. ............ 424/458 |
| 6,627,223 | B2 | 9/2003 | Percel et al. |
| 2002/0012675 | A1 * | 1/2002 | Jain et al. ............... 424/400 |
| 2004/0192690 | A1 | 9/2004 | Buxton et al. |
| 2005/0032799 | A1 | 2/2005 | Buxton et al. |

FOREIGN PATENT DOCUMENTS

| WO | WO 92/13527 | 8/1992 |
|---|---|---|
| WO | WO 97/14415 | 4/1997 |
| WO | WO03090693 A2 * | 11/2003 |

* cited by examiner

*Primary Examiner* — Robert A Wax
*Assistant Examiner* — Bethany Barham
(74) *Attorney, Agent, or Firm* — Hedman & Costigan, P.C.; James V. Costigan

(57) ABSTRACT

Rapidly disintegrating multiparticulate controlled release formulations of lamotrigine having an improved pharmacokinetic profile and improved patient compliance, and process of preparing the formulations. It provides better control of blood plasma levels than conventional tablet formulations that is administered once or more times a day.

20 Claims, No Drawings

CONTROLLED RELEASE FORMULATION OF LAMOTRIGINE

FIELD OF THE INVENTION

The invention relates to rapidly disintegrating multiparticulate controlled release formulations of lamotrigine having an improved pharmacokinetic profile resulting in reduced dosing frequency. This invention further relates to a process for preparing the dosage form.

BACKGROUND OF THE INVENTION

Controlled release refers to the release of the therapeutically active agent from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to predetermined profile. Such release rates can provide therapeutically effective levels of an agent for an extended period of time and thereby provide a longer period of pharmacological or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bio-availability, convenience, and patient compliance, as well as minimizing side effects associated with inappropriate immediate release rates such as high initial release rate and, if undesired, uneven blood or tissue levels.

Lamotrigine, an antiepileptic drug of the phenyltriazine class is chemically unrelated to existing antiepileptic drug. Its chemical name is 3,5-diamino-6(2,3-dichlorophenyl)-1,2,4-triazine, its molecular formula is $C_9H_7N_5Cl_2$. It is disclosed in EP-A-0021121, which is incorporated by reference.

Lamotrigine has been used to treat over a million patients worldwide, including about 4000 adults and over 1000 children in clinical trials, Extensive experience with lamotrigine has indicated that it may be effective when other anticonvulsant drugs have failed. It is a valuable broad-spectrum drug that is well tolerated and has few adverse effects apart from skin rash (Besag FMC, CNS Drugs 2000). Pharmacokinetically, the plasma concentrations of lamotrigine vary linearly with the dose (Ramsay RE, 1991).

Over the range 50 to 400 mg as a single dose, $C_{max}$ increases proportionately from 0.58 to 4.63 µg/ml, as does the AUC (29.9 to 211.9 mg/L.h). Acute and chronic studies in humans have suggested that lamotrigine levels of 1-3 µg/ml are effective in controlling seizures (Betts et al, 1991). Adverse events associated with lamotrigine are typical of antiepileptic drugs, namely dizziness, ataxia, diplopia, somnolence, headache, and asthenia. The incidence of such side effects is around 10% (Ramsay RE, 1991), Overall, 8.6% of patients were removed from clinical trials because of adverse experiences that included, in addition to rash, nausea/vomiting and intolerable episodes of the CNS-related events (Ramsay RE, 1991; Goa K L et al, 1993).

Neurological side effects are normally seen at higher plasma concentrations (which are most likely to occur at peak plasma concentrations). During the first 18 weeks of lamotrigine treatment 16.7% of patients reported nausea and vomiting at a mean concentration of 6.00 to 7.99 µg/ml and 100% reporting headache and ataxia at >10 µg/ml (Goa K L et al, 1993). Similarly, Binnie et al., (1987) reported side effects only in patients with levels above 3 µg/ml.

Dose reduction and slow dosage escalation are two techniques to overcome these peak time side effects (Binnie et al, 1987). The present invention will reduce these side effects by controlling the $C_{max}$ of lamotrigine by the use of a novel controlled release formulation of lamotrigine. It will also maintain the steady state concentration with little fluctuations. The reduced incidence of these neurological side effects will improve patient compliance with the therapy.

Serious skin reactions (including Steven Johnson Syndrome and Toxic Epidermal Necrolysis) occurring in patients taking lamotrigine were highlighted by the Committee of Safety Medicine (CSM) in 1997 and have subsequently been discussed in the literature (Mitchell P, 1997; Anon., Drug and Therapy Perspectives, 1998). Rash, which has occurred in 10% of patients in placebo-controlled trials has led to discontinuation of therapy in 1% of patients (most common cause of discontinuation) (Besag FMC, CNS Drugs 2000). Skin reactions such as Stevens Johnson Syndrome are potentially fatal and have an incidence of 1 in 1000 person-years in adults. The incidence is higher in children. Risk factors for skin reactions include high plasma concentration, concomitant sodium valproate therapy (Valproate reduces the hepatic clearance of lamotrigine thereby increasing plasma concentrations of the drug by approximately two fold for a given dose), a high initial dose of lamotrigine and rapid dose escalation (Mitchell P, 1997; Anon., Current Problems in Pharmacovigilance).

There is some preliminary data that shows that slow dosage escalation or titration when initiating therapy may lessen the likelihood of development of severe rash (Ramsay RE, 1991). Controlled release lamotrigine, which is designed to avoid excessive $C_{max}$ levels, will produce lower plasma concentrations which are reached over a longer period of time and will reduce the incidence of this troublesome side effect of lamotrigine. Further, the controlled release formulation will be much safer to use with concomitantly administered drugs such as phenytoin, carbamazepine, sodium valproate etc.

Presently lamotrigine is prescribed in conventional tablets or dispersible/chewable tablet form in doses ranging from 25 to 600 mg/day, once a day or two divided doses. Immediate release dosage forms provide rapid dissolution results with a rapid increase in blood plasma levels after each dosing, which causes adverse effects. The reasons for giving divided doses of lamotrigine is to prevent very high concentrations in the plasma, which can occur with single daily dose of conventional formulation.

It is a known fact that frequent dosing results in poor patient compliance resulting in an inadequate/sub-optimal therapeutic effect.

Peak trough fluctuations at steady state are reduced whenever one or more of the following occur:
Increase in half-life.
Shorter dosing interval
Reduced rate of absorption.

The oral administration of solid dosage forms, for example tablets, capsules, often presents ingestion problems for the patient, especially in case of children or old people. In order to get around this problem other forms of pharmaceutical formulations are resorted to, for example chewable tablets, dispersible tablets and monodose sachets, the contents of which are to be dissolved or suspended in water and taken orally.

The problems inherent in the administration of divided doses of lamotrigine point to the desirability of providing a controlled release formulation of lamotrigine, which can be given once daily to improve the patient compliance, which can be taken without water or can be dispersed in water for the convenience of the patients and can provide an improved pharmacokinetic profile. Improved pharmacokinetic profile here means that the formulation will provide a more constant blood level of drug and will show less fluctuation between the maximum and minimum plasma drug concentration than once or repeated doses of regular/immediate release drug formulation containing equal amounts of active ingredients administered per day.

Formulations according to this aspect of the present invention are particularly useful in administration of medications to individuals who cannot or will not chew or swallow, such as debilitated patients, patients who have difficulty swallowing solids, and the elderly. Furthermore, the formulations according to the invention provide a further significant advantage with respect to tablet or simple capsule. People who need to swallow a tablet or a capsule under the above mentioned conditions may sometimes have to swallow the said tablet or capsule without water and that can be dangerous as the tablet or capsule can get into trachea i.e. respiratory site.

The prior art discloses many different types of multiple unit dosage forms. An example of a controlled release dosage form, which releases the active substance by diffusion through a membrane, is described in U.S. Pat. No. 4,927,640, i.e. a multiple unit system containing small inert cores with an active substance and a release controlling polymeric membrane. The mechanical properties of such multiple units formulated into tablets are reported in Pharmaceutical Research, 10 (1993), p. 274. There are examples in prior art which disclose that pellets may be formulated into tablets, there are no examples describing any compositions of such a tablet formulation or a technique to manufacture such a formulation comprising lamotrigine which is given once a day and provided improved pharmacokinetic profile.

SUMMARY OF THE INVENTION

The invention provides a multiparticulate controlled release dosage formulation of lamotrigine, which comprises:
(a) particles, which comprise lamotrigine;
(b) a release rate controlling polymer; and
(c) a rapidly disintegrating binder, which will allow the particles to rapidly disperse in an aqueous environment.
Preferred dosage forms will comprise discrete pelleted cores covered with a rate controlling membrane where the core has either a spheronized homogeneous core or a heterogeneous core, which comprises an inert base having layers of drug applied by a suitable coating procedure. The particle may be placed in a tablet form or they may be placed in a hard gelatin capsule.

Therefore, it is a primary object of the present invention to provide a novel lamotrigine dosage form that will improve patient compliance by (a) providing a rapidly disintegrating formulation that will disperse in the mouth for ease of administration or in water (b) will reduce the dosage frequency to once daily and (c) will provide a pharmacokinetic profile that will reduce or eliminate neurological side effects and/or skin reactions.

It is also an object of the invention to provide a dosage form of lamotrigine that will control the release of lamotrigine in such a manner that an effective concentration in the blood can be maintained over an extended period of time, but also the drug release should be such that the drug concentration in the blood remains relatively constant over the extended period of time to improve therapeutic results and/or minimize the side effects.

DETAILED DESCRIPTION OF THE INVENTION

The pharmaceutrical composition prepared according to the instant invention is suitable for reducing fluctuation in troughs and peaks of drug concentration in patient's blood plasma wherein the ratio of peak and trough is in the range of 1.0 to 1.6.

Further, the pharmaceutical composition of the instant invention will reduce the side effects of lamotrigine and will also reduce the dosing frequency to once daily. It will also be safer than conventional lamotrigine, when given in combination with other antiepileptic drugs selected from the group comprising phenytoin, carbamazepine, sodium valproate etc. The side effects mentioned above are ataxia, diplopia, somnolence, headache, and rash.

The core (core particle) may comprise lamotrigine or a pharmaceutically acceptable salts thereof along with commonly used water soluble and/or water insoluble and/or water dispersible and/or water disintegrable excipients and optionally comprising lamotrigine or pharmaceutically acceptable salts thereof with rate controlling excipient(s). The lamotrigine and the excipient(s) are preferably present in a ratio of from 1:100 to 100:1, more particularly from 1:20 to 20:1 and most preferably from 10:1 to 1:10 or in the alternative a ratio of 5:1 to 1:5 may be used.

The core can optionally comprise an acid, preferably an organic acid and the ratio of lamotrigine and organic acid is from 50:1 to 1:50 or more preferably for 20:1 to 1:1 and most preferably 10:1 to 2:1.

The organic acid, when such is used, is preferably selected from adipic acid, ascorbic acid, fumaric acid, citric acid, malic acid, succinic acid and tartaric acid.

The active ingredient can be present in the form of a free base or in the form of pharmaceutically acceptable salt such as hydrochloride or maleate salt. Further, the active ingredient, where applicable, may be present either in the form of one substantially optically pure enantiomer or as a mixture of enantiomers or polymorphs thereof.

The lamotrigine and excipient(s) are preferably built up on a central inert nucleus. The inert nucleus suitability consists of an inert component such as a non-pareil bead of sugar, sugar/starch or microcrystalline cellulose (Celphere R.T.M.) having an average diameter in the range of from 0.05 to 0.75 mm, typically from 0.15 to 0.3 mm. The actual nucleus size used may vary depending on the drug loading required for particular formulation. The core maybe built up in a conventional coating pan. Alternatively, the drug and polymeric material may be built up on a central inert nucleus as herein before defined in an automated coating system for example, a Wurster coater. The core may also include further components to those specified above such as dispersing agent, glidant and/or surfactant.

According to one embodiment the rate-controlling membrane is made up of pharmaceutically acceptable polymer(s) of varying water solubility or water permeability. The rate controlling membrane can be combination of polymers such as polymers of low water permeability/solubility polymer(s) and high permeability/solubility polymer(s).

The polymers that can be used to form the rate-controlling membrane or micromatrix are described in greater detail herein below. The rate controlling polymer(s) are selected from the group comprising alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene terephthalates, polyvinyl esters, polyvinylpyrrolidone, polyglycolides, polysiloxanes and polyurethanes and co-polymers thereof. Examples of suitable polymer are described in Kibbe, Handbook of Pharmaceutical Excipients, Third Ed. (2000)pp. 401-406.

According to an especially preferred embodiment, the rate controlling polymers contain ammonio methacrylate co-polymers as hereinafter described. These high water soluble/permeable polymers include polymers such as Eudragit RL. Likewise, the term low water soluble/permeable polymer as used herein includes polymers, such as Eudragit RS.

The high water soluble/permeable polymer that are suitable are selected from the group comprising polyvinyl alcohol, polyvinylpyrrolidone, methylcellulose, hydroxypropylcellulose, hydroxypropylmethyl cellulose or polyethylene glycol, or a mixture thereof.

The low water soluble/permeable polymer that are suitable are selected from the group comprising ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate). Poly(isodecyl methacrylate), poly(lauryl methacrylate); poly(phenyl methacrylate), poly(methyl acrylate), poly(isopropyl acrylate), poly(isobutyl acrylate), poly(octadecyl acrylate), or a mixture thereof.

A suitable polymer, which is freely permeable to aqueous solution of lamotrigine and water, is a polymer sold under the Trade Mark Eudragit RL. The suitable polymers, which are slightly permeable to aqueous solution of lamotrigine and water, are polymers sold under the Trade Mark Eudragit RS and Eudragit NE 30D or a polymer whose permeability is pH dependent such as those sold under the trade marks Eudragit L, Eudragit S or Eudragit E.

The methacrylate co-polymers are preferably selected from the group consisting of Eudragit RS which is poly(ethyl acrylate, methyl methacrylate, trimethylammonioethyl methacrylate chloride) 1:2:0.1; Eudragit RL which is poly(ethyl acrylate, methyl methacrylate, trimethylamonioethyl methacrylate chloride) 1:2:0.2; Eudragit L30D 55 which is polmethacrylic acid, ethyl acrylate 1:1; Eudragit NE30D which is poly(ethyl acrylate, methyl methacrylate) 1:1.

Eudragit RL is highly permeable and Eudragit RS and Eudragit NE 30D low permeable polymers, independent of pH. Eudragit L is an anionic polymer synthesized from methacrylic acid and methacrylic acid methyl ester. It is insoluble in acids and pure water. It becomes soluble in neutral to weakly alkaline conditions. The permeability of Eudragit L. is pH dependent. Above pH 5.0, the polymer becomes increasingly permeable. (Eudragit L is described in the "Eudragit L" brochure of Rohm Pharma GmbH (1986)).

The polymeric coating used to form the rate-controlling membrane can also include one or more commonly used excipients in oral pharmaceutical formulations. Representative commonly used excipients in oral pharmaceutical formulations are selected from the group comprising talc, fumed silica, glyceryl monostearate, magnesium stearate, calcium stearate, kaolin, colloidal silica, gypsum, Tween 80, Syloid 244FP R.T.M.,Geleol pastiles, micronised silica and magnesium trisilicate.

The quantity of commonly used excipients in the lamotrigine oral formulations is from about 0.1 to about 200% by weight, preferably from 0.25 to 100% and more particularly 0.3 to 75% based on the total dry weight of the polymer.

The polymeric coating can also include a material that improves the processing of the polymers. Such materials are generally referred to as "plasticisers" and include, for example, adipates, azelates, benzoates, citrates, isobutyrates, phthalates, sebacates, stearates, tartrates, polyhydric alcohols and glycols. Representative plasticisers include acetylated monoglycerides; butyl phthalyl butyl glycolate; dibutyl tartrate; diethyl phthalate; diethyl phthalate; ethyl phthalyl ethyl glycolate; glycerin; ethylene glycol, propylene glycol; triethyl citrate; triacetin, triproprinon; diacetin; dibutyl phthalate; acetyl monoglyceride; polyethylene glycols; castor oil; triethyl citrate; polyhydric alcohols, acetate esters, glycerol triacetate, acetyl triethyl citrate, dibenzyl phthalate, dihexyl phthalate, butyl octyl phthalate, di-isononyl phthalate, butyl octyl phthalate, dioctyl azelate, epoxidised tallate, triisoctyl trimellitate, diethylexyl phthalate, di-n-octyl phthalate, di-l-octyl phthalate, di-l-decyl phthalate, di-n-undecyl phthalate, di-n-tridecyl phthalate, tri-2-ethylexyl trimellitate, di-2-ethylexyl adipate, di-2-ethylhexyl sebacate, di-2-ethyhexyl azelate, dibutyl sebacate, glyceryl monocaprylate and glyceryl monocaprate.

The amount of plasticizer to be used is from about 1% to 60% based on the weight of the dry polymer(s),more preferably 5% to 60%. The polymeric coating can also include an anti-foaming agent to prevent foaming during the process. An example of an anti-foaming agent is Simethicone. The amount of anti-foaming agent to be used in the coating is preferably from 0% to 0.5% of the final coating formulation.

The amount of polymer(s) to be used in forming the particles will be determined based on various parameters such as the desired delivery properties, including the amount of drug to be delivered, the drug release rate desired, and the size of the particles. The rate controlling membrane on the particles, including all solid components thereof such as copolymer, filler, plasticizer and optional commonly used excipients and processing aids, is from about 1% to 150% weight gain on the cores, preferably 5% to 80% weight gain and more preferably 5% to 60% weight gain on the cores. The rate controlling polymer membrane can be coated by any known method, including spray application. Spraying can be carried out using a fluidized bed coated (preferably Wurster coating), or in a pan coating system.

The core is suitably coated with a polymeric rate-controlling membrane comprising at least one polymeric material as described above. The core may be coated to a coating level that is sufficient to facilitate the desired release rate.

The rate-controlling membrane can comprise a single polymer or a mixture of two or more polymers.

Oral controlled release formulations of the invention can be in the form of a suspension made with suitable commonly used suspending agents and other auxiliary pharmaceutical excipients.

The rate controlling polymer of the membrane is any one of those herein above specified for the core and includes polymers with varying solubility and permeability to water.

The oral controlled release lamotrigine formulation of the invention can be in the form of a multiparticulate formulation or a tablet. The term "multiparticulate" as used herein includes discrete particles such as nanoparticles, microspheres, microcapsules, pellets, mini-tablets, granules, beads, spheronized granules and mixtures or combinations thereof. A multiparticulate oral dosage form according to the invention can comprise a blend of one or more populations of particles, pellets or mini-tablets having different in vitro and/or in vivo release characteristics. For example, the multiparticulate oral dosage form can comprise a blend of an instant or fast release component and controlled release component compressed into a rapidly disintegrating tablet. Fast release components and/or controlled release components can additionally be coated with an enteric coating polymer membrane. Alternatively the blend of instant or fast release and controlled release component contained in a suitable capsule, for example hard or soft gelatin capsules. The multiparticulate formulation may be filled into a capsule and may be administered by swallowing the capsule or by opening said capsule and sprinkling the contents onto food. Alternatively the multiparticulate formulation may be presented in a sachet or other binder that rapidly releases in an aqueous environment.

The particles and one or more auxiliary excipient materials can be compressed into tablet form such as a single or multiple layer tablets. Typically a multiple layer tablet may comprise two layers, which may contain the same or different levels of the same active ingredient having the same or different release characteristics, or may contain different release characteristics.

As indicated above the oral controlled release lamotrigine formulations of the present invention may comprise auxiliary excipients such as for example diluents, lubricants, surfactants, disintegrants, plasticisers, anti-tack agents, opacifying agents, pigments, flavourings and such like. As will be appreciated by those skilled in the art, the exact choice of excipient and their relative amounts will depend to some extent on the final oral dosage form into which the controlled release lamotrigine formulation is incorporated.

The amount of the auxillary excipients may comprise from 0.05 to 75 weight % based on the total weight of the formulation, depending on the desired property to be imparted to the formulation.

Suitable diluents include for example pharmaceutically acceptable inert fillers such as microcrystalline cellulose, lactose, dibasic calcium phosphate, saccharides, and/or mixtures of the foregoing.

Examples of diluents include microcrystalline celluloses such as those sold under the Trade Mark Avicel pH 101, Avicel pH 102, Avicel pH 112, Avicel pH 200, Avicel pH 301, and Avicel pH 302; lactose such as lactose monohydrate, lactose anhydrous and Pharmatose DCL21 (Pharmatose is a trade mark), including anhydrous, monohydrate and spray dried forms; dibasic calcium phosphate such as Emcompress (Emcompress is a Trade Mark); mannitol; Pearlitol SD 200 (Pearlitol SD 200 is a trade mark); starch; sorbitol; sucrose; and glucose.

The amount of the diluents may comprise from 1 to 80 weight % based on the total weight of the formulation, and preferably from 20 to 75 weight % of the formulation based on the total weight of the formulation.

Rapidly disintegrating binders may include, for example, crospovidone, microcrystalline cellulose, sodium starch glycolate, croscarmellose sodium starch, sodium carboxy methyl cellulose, pregelatinized starch which are used in effective amounts to act as a binder for lamotrigine and any added excipients which are used in effective amounts to act as binders for the lamotrigine and any added excipients. Suitable lubricants, including agents that act on the flowability of the powder to be compressed are, for example, colloidal silicon dioxide such as Aerosil 200 (Aerosil is a Trade Mark); talc; stearic acid, magnesium stearate, calcium stearate and sodium stearyl fumarate.

Suitable disintegrants include for example lightly crosslinked polyvinyl pyrrolidone, corn starch, potato starch, maize starch and modified starches, croscarmellose sodium, crosprovidone (Polyplasdone XL 10 R.T.M.), sodium starch glycolate and combinations and mixtures thereof.

The disintegrants may comprise from 1 to 20 weight % of the formulation and the lubricants may comprise from 0.05 to 10 weight % of the formulation.

The dissolution of the controlled release lamotrigine may be determined by the following method.

| Instrument | Apparatus II, USP (Paddle) |
|---|---|
| Revolution | 50/min. |
| Temperature | 37 ± 0.5° C. |
| Dissolution mediums | Medium 1: 900 ml 0.1 N HCl (analyzed at wavelength 265 nm), Medium 2) 900 ml pH 4.5 buffer (analyzed at wavelength 270 nm), Medium 3) 900 ml pH 6.8 buffer (analyzed at wavelength 305 nm), Medium 4) 900 ml pH 7.5 buffer (analyzed at wavelength 305 nm), Medium 5) 750 ml 0.1 N HCl (analyzed at wavelength 267 nm) for 1 hour then for remaining intervals 250 ml. of trisodium phosphate buffer was added to it and pH adjusted to 6.8 (analyzed at wavelength 305 nm). Lamotrigine was determined using a UV Spectrophotometer. |

In the appended Examples, the above described dissolution test was used to determine the release rates of the particular dosage forms.

DESCRIPTION OF THE PREFERRED EMBODIMENTS

The following examples further illustrate but by no means limit the present invention.

Example 1

1) Production of Core

A fluidized bed processor of Wurster type (manufactured by Glatt, Germany), GPCG-3 was charged with 750 gm of microcrystalline cellulose (Celphere CP 102 R. T.M.) (Particle diameter of 0.15 to 0.30 mm), it was coated by spraying a bulk liquid of the following composition prepared in advance. The spraying operation was stopped when the specified amount of bulk liquid had been sprayed, and then drying was carried in the fluid bed processor. The resulting granules (core particles) were sieved through sieve 425 μm and 180 μm to provide 1750 g granules (core particles). The over size and under size core particles were discarded.

Bulk Liquid

| Lamotrigine | 900.00 g |
|---|---|
| Hydroxypropyl Methylcellulose E-15 LV | 545.45 g |
| Purified Water | 13.20 kg. |

2) Production of Controlled Release Particles

A fluidized bed processor of Wurster type (manufactured by Glatt, Germany), GPCG-3 was charged with 1500 g of above drug granules (core particles). A controlled release rate controlling membrane coating liquid of following composition prepared in advance was sprayed. The coated particles were dried in a stream of hot air in tray drier and sifted through 425 μm and 180 μm sieves to provide 1750 g of controlled release particles. The over size and under size controlled release particles were discarded.

Rate Controlling Coating Membrane Composition

| | |
|---|---|
| Eudragit RS PO | 187.25 |
| Eudragit RL PO | 9.848 g |
| Triethyl citrate | 39.425 g |
| Talc | 63.45 g |
| Methylene Chloride | 1140.0 g |
| Isopropyl alcohol | 1910.0 g |

Example 2

Example 1 was repeated except that the composition of controlled release rate controlling coating membrane was as follows:

Rate Controlling Coating Membrane Composition

| | |
|---|---|
| Eudragit RS PO | 163.84 g |
| Eudragit RL PO | 8.617 g |
| Triethyl citrate | 34.5 g |
| Talc | 55.52 g |
| Methylene Chloride | 997.5 g |
| Isopropyl alcohol | 1671.25 g |

The dissolution rate of the controlled release particles was determined (Table 1) was determined (Table 1)

TABLE 1

Dissolution profile

| Medium → Time (Hour) | 1 | 2 | 3 | 4 | Medium → Time (Hour) | 5 |
|---|---|---|---|---|---|---|
| | % Release | | | | | % Release |
| 1 | 46.66 | 68.12 | 41.53 | 44.43 | 1 | 49.4 |
| 2 | 66.06 | 80.82 | 54.08 | 55.42 | 2 | 62.3 |
| 4 | 85.53 | 82.77 | 63.9 | 57.13 | 3 | 69.1 |
| 6 | 93.19 | 92.61 | 69.37 | 71.28 | 5 | 80.1 |
| 8 | 98.05 | 100.09 | 77.88 | 78.75 | 7 | 85.5 |
| 10 | 101.23 | 100.86 | 82.88 | 87.38 | 9 | 91.5 |
| 12 | 100.86 | | 83.84 | 89.68 | 11 | 94.6 |
| 14 | | | 87.81 | 91.29 | 13 | 97.2 |
| 24 | | | 92.82 | 94.47 | 25 | 108.9 |

In an oral bioavailability study carried out at the pharmacokinetic unit (PKU), controlled release (CR) formulation of lamotrigine (50 mg) (encapsulated controlled release particles of example 2) and the conventional formulation (100 mg) were administered in human subjects. The plasma concentrations of lamotrigine (Table 2) and the resulting pharmacokinetic parameters are presented in Table 3.

TABLE 2

Plasma concentration-time profile formulation of Lamotrigine

| | Plasma concentration (μg/ml) Mean ± SD | |
|---|---|---|
| Time (Hour) | Conventional Tablet 100 mg | Controlled Release Formulation (example 2) 50 mg |
| 0.00 | 0.000 ± 0.000 | 0.000 ± 0.000 |
| 0.25 | 0.436 ± 0.460 | |
| 0.50 | 1.064 ± 0.593 | 0.000 ± 0.000 |
| 1.00 | 1.220 ± 0.309 | 0.000 ± 0.000 |
| 1.50 | 1.251 ± 0.221 | 0.098 ± 0.106 |
| 2.00 | 1.346 ± 0.156 | 0.172 ± 0.113 |
| 2.50 | 1.310 ± 0.154 | |
| 3.00 | 1.261 ± 0.157 | 0.314 ± 0.135 |
| 3.50 | 1.225 ± 0.156 | |
| 4.00 | 1.199 ± 0.139 | 0.376 ± 0.122 |
| 5.00 | | 0.410 ± 0.137 |
| 6.00 | 1.134 ± 0.121 | |
| 7.00 | | 0.409 ± 0.105 |
| 8.00 | 1.050 ± 0.137 | |
| 9.00 | | 0.435 ± 0.117 |
| 12.00 | 0.967 ± 0.157 | 0.391 ± 0.122 |
| 15.00 | | 0.363 ± 0.105 |
| 16.00 | 0.857 ± 0.165 | |
| 18.00 | | 0.368 ± 0.094 |
| 21.00 | | 0.343 ± 0.112 |
| 24.00 | 0.843 ± 0.186 | 0.353 ± 0.088 |
| 36.00 | | 0.281 ± 0.109 |
| 48.00 | 0.519 ± 0.209 | 0.210 ± 0.086 |
| 72.00 | 0.309 ± 0.184 | 0.138 ± 0.088 |
| 96.00 | 0.203 ± 0.158 | 0.085 ± 0.053 |

TABLE 3

Pharmacokinetic parameters of formulation of Lamotrigine

| Kinetic Parameter | Conventional Tablet 100 mg | Controlled Release Formulation (example 2) 50 mg |
|---|---|---|
| AUC (0-inf) trap (μ/ml) * hr | 71.123 | 26.719 |
| T ½ hr | 36.731 | 34.702 |
| Kel hr$^{-1}$ | 0.023 | 0.021 |
| Cmax μg/ml | 1.494 | 0.446 |
| Tmax hr | 1.656 | 7.667 |

Example 3

Example 1 was repeated except that the rate controlling coating membrane composition was as follows:

| | |
|---|---|
| Eudragit RS 30D | 537.25 g |
| Eudragit RL 30D | 33.425 g |
| Eudragit NE 30D | 133.758 g |
| Triethyl citrate | 40.133 g |
| Tween 80 | 1.05 g |
| Geleol Pastilles | 10.5 g |
| Purified Water | 435.166 g |

The dissolution rate of the controlled release particles was determined (Table 4)

TABLE 4

| Medium → Time (Hour) | 1 | 2 | 3 | 4 | Medium → Time (Hour) | 5 |
| --- | --- | --- | --- | --- | --- | --- |
| | % Release | | | | | % Release |
| 1 | 60.05 | 73.94 | 47.33 | 47.69 | 1 | 51.2 |
| 2 | 83.24 | 89.55 | 64.01 | 64.95 | 2 | 79.6 |
| 4 | 97.33 | 92.3 | 77.34 | 69.24 | 3 | 84.5 |
| 6 | 98.91 | 92.43 | 87.24 | 84.83 | 5 | 89.0 |
| 8 | 100.61 | 100.41 | 95.22 | 94.14 | 7 | 94.5 |
| 10 | 104.69 | 101.41 | 97.08 | 97.48 | 9 | 96.5 |
| 12 | | | 97.92 | 99.9 | 11 | 101.3 |
| 14 | | | 102.25 | 100.12 | 13 | 102.1 |
| 24 | | | | 102.44 | 25 | 107.1 |

Example 4

Production of Dispersible Tablets

To 329.8 of controlled release particles of example 3 added 493.5 g microcrystalline cellulose (Avicel PH 200 R. T. M.), 26.25 g of crospovidone (Polyplasdone XL10 R.T.M.), 8.75 g of talc, 4.375 g of Magnesium Stearate and 4.375 g of Colloidal Silicon dioxide, which was admixed in a bag to give mixed powders. 862.5 g of above mixed powder were tableted using Korsch Compression Machine with a punch having beveled edges, 7.98 mm in diameter to provide tablets each weighing 347 mg.

The hardness and disintegration time of each tablet thus obtained was 70-100N and 20-30 seconds respectively.

The dissolution rate of tablets was estimated (Table 5)

TABLE 5

| Medium → Time (Hour) | 5 % Release |
| --- | --- |
| 1 | 59.8 |
| 2 | 78.5 |
| 3 | 83.5 |
| 5 | 87.5 |
| 7 | 89.1 |
| 9 | 90.6 |
| 11 | 92.6 |
| 13 | 93.3 |

Example 5

Example 1 was repeated except that the rate controlling coating membrane composition was as follows:

| Eudragit NE 30D | 208.222 g |
| --- | --- |
| Triethyl citrate | 9.311 g |
| Geleol pastilles | 2.910 g |
| Tween 80 | 0.291 g |
| Purified Water | 114.000 g |

The dissolution rate of the controlled release particles was determined (Table 6)

TABLE 6

| Medium → Time (Hour) | 5 % Release |
| --- | --- |
| 1 | 60.5 |
| 2 | 79.2 |
| 3 | 85.96 |
| 5 | 90.18 |
| 7 | 92.16 |
| 9 | 92.92 |
| 11 | 96.08 |
| 13 | 98.4 |
| 25 | 101.93 |

Example 6

Example 1 was repeated except that the rate controlling coating membrane composition was as follows:

| Eudragit NE 30D | 728.777 g |
| --- | --- |
| Triethyl citrate | 32.588 g |
| Geleol Paspilles | 10.188 g |
| Tween 80 | 1.018 g |
| Purified Water | 399.000 g |

The dissolution rate of the controlled release particles was determined (Table 7).

TABLE 7

| Medium → Time (Hour) | 5 % Release |
| --- | --- |
| 1 | 8.7 |
| 2 | 22.01 |
| 3 | 31.38 |
| 5 | 41.87 |
| 7 | 44.86 |
| 9 | 50.14 |
| 11 | 52.4 |
| 13 | 59.32 |
| 25 | 67.91 |

Example 7

Example 1 was repeated except that the rate controlling coating membrane composition was as follows:

| Eudragit NE 30D | 833.0 g |
| --- | --- |
| Triethyl citrate | 37.2 g |
| Geleol Pastilles | 11.66 g |
| Tween 80 | 1.166 g |
| Purified Water | 585.9 g |

The dissolution rate of the controlled release particles was determined (Table 8).

TABLE 8

| Medium → Time (Hour) | 5 % Release |
| --- | --- |
| 1 | 9.7 |
| 2 | 25.58 |
| 3 | 34.65 |
| 5 | 44.87 |

TABLE 8-continued

| Medium → Time (Hour) | 5 % Release |
|---|---|
| 7 | 49.52 |
| 9 | 51.96 |
| 11 | 52.25 |
| 13 | 58.51 |
| 25 | 62.08 |

Example 8

Production of Dispersible Tablets

To 104.55 g of controlled release particles of example 6 added 227.95 g Avicel PH 200, 10.50 g of crospovidone (Polyplasdone XL10 R.T.M.), 3.50 g of talc, 1.75 g of Magnesium Stearate and 1.75 g of Colloidal Silicon dioxide, which was admixed in a bag to give mixed powders. 350 g of above mixed powder were tabletted using a Korsch Compression Machine with a punch having beveled edges, 7.98 mm in diameter to provide tablets each weighing 350 mg.

The hardness and disintegration time of each tablet thus obtained was 100-120N and 10-15 seconds respectively.

The dissolution rate of tablets was estimated (Table 9).

TABLE 9

| Medium → Time (Hour) | 5 % Release |
|---|---|
| 1 | 34.3 |
| 2 | 56.1 |
| 3 | 65.9 |
| 5 | 73.9 |
| 7 | 82.9 |
| 9 | 92 |
| 11 | 93.5 |
| 13 | 97 |
| 25 | 100.2 |

Example 9

Production of Dispersible Tablets

To 45.95 g of controlled release particles of example 5 and 54.54 g of controlled release particles of example 7 added 232.51 g Avicel PH 200, 10.50 g of crospovidone (Polyplasdone XL10 R.T.M.), 3.50 g of talc, 1.75 g of Magnesium Stearate and 1.75 g of Colloidal Silicon dioxide, which was admixed in a bag to give mixed powders. 350 g of above mixed powder were tableted using Korsch Compression Machine with a punch having beveled edges, 7.98 mm in diameter to provide tablets each weighing 350 mg.

The hardness and disintegration time of each tablet thus obtained was 80-110N and 10-20 seconds respectively.

The dissolution rate of tablets was estimated (Table 10).

TABLE 10

| Medium → Time (Hour) | 1 | 2 | 3 | 4 | Medium → Time (Hour) | 5 % Release |
|---|---|---|---|---|---|---|
| | % Release | | | | | |
| 1 | 44.4 | 23.8 | 21.4 | 20.4 | 1 | 49.8 |
| 2 | 58.6 | 37.7 | 35.4 | 36.5 | 2 | 60.2 |
| 4 | 71.5 | 53.5 | 45.3 | 46.5 | 3 | 67.2 |
| 6 | 77.1 | 60.9 | 57.7 | 52 | 5 | 74.2 |

TABLE 10-continued

| Medium → Time (Hour) | 1 | 2 | 3 | 4 | Medium → Time (Hour) | 5 % Release |
|---|---|---|---|---|---|---|
| | % Release | | | | | |
| 8 | 85.1 | 71 | 61.4 | 57.8 | 7 | 79.2 |
| 10 | 89.6 | 79 | 65.1 | 61.8 | 9 | 81.1 |
| 12 | 93 | 81.3 | 68 | 65.8 | 13 | 82.1 |
| 24 | 94 | 99.1 | 86.5 | 74.3 | 25 | 86 |

Example 10

Production of Capsules

Controlled release particles of example 5 (45.45 mg/capsule) and 7 (54.54 mg/capsule) were filled in capsules The dissolution rate of capsules was estimated (Table 11)

TABLE 11

| Medium → Time (Hour) | 1 | 2 | 3 | 4 | Medium → Time (Hour) | 5 % Release |
|---|---|---|---|---|---|---|
| | % Release | | | | | |
| 1 | 37.03 | 16.69 | 19.04 | 15.92 | 1 | 41.3 |
| 2 | 55.4 | 27.54 | 31.9 | 28.85 | 2 | 54.75 |
| 4 | 75.96 | 42.42 | 43.38 | 43.49 | 3 | 59.84 |
| 6 | 83.82 | 47.72 | 53.45 | 50.50 | 5 | 68.39 |
| 8 | 91.27 | 58.93 | 57.66 | 56.02 | 7 | 73.41 |
| 10 | 94.39 | 63.76 | 61.87 | 62.65 | 9 | 76.05 |
| 12 | 96.87 | 66.53 | 65.5 | 64.06 | 11 | 78.09 |
| 24 | 97.98 | 85.79 | 79.9 | 75.81 | 13 | 81.66 |
| | | | | | 25 | 84.69 |

Example 11

1) Production of Core

A Wurster type fluidized bed (manufactured by Glatt, Germany) GPCG-3 was charged with 700 g. of microcrystalline cellulose (Celphere CP 102 R.T.M.)(Particle diameter Of 0.15 to 0.3 mm). The microcrystalline cellulose was coated by spraying a bulk liquid which was prepared in advance. The spraying operation was stopped when the specified amount of bulk liquid had been sprayed, and then drying was carried out in the fluid bed processor. The resulting granules (core particles) were sieved through sieve 425 μm and 180 μm to provide 2813 g of granules. The over size and under size core particles were discarded. Due to the constraint of equipment capacity, the coating was done in parts.

Bulk Liquid

| Lamotrigine | | 2.0 kg |
|---|---|---|
| Hydroxypropyl Methylcellulose | 6 cps | 0.3 kg |
| Povidone (PVP K-90) | | 0.3 kg |
| Purified Water | | 10.0 kg |

2) Production of Controlled Release Particles

A fluidized bed Wurster coater (Glatt, Germany, GPCG-3) was charged with 1500 g of the granules (core particles) prepared in step 1. A controlled release rate controlling membrane coating of following composition, prepared in advance, was sprayed. The coated particles were dried in a stream of hot air in a tray drier and sifted through 425 μm and 180 μm sieves to provide 1910 g of controlled release particles. The oversize and under size controlled release particles were discarded.

Rate Controlling Coating Membrane Composition:

| Eudragit RS 30D | 1072.67 g |
|---|---|
| Eudragit RL 30D | 107.26 g |
| Triethyl citrate | 152.28 g |
| Silicon dioxide (Syloid 244FP R.T.M.) | 94.6 g |
| Purified Water | 800 g |

3) Production of Dispersible Tablets

To 355.36 g of the controlled release particles that were prepared above in 2, the following ingredients were added: 857.01 g of mannitol (Pearlitol SD 200 R.T.M.), 67.5 g of crospovidone (Polyplasdone XL10 R.T.M.), 13.5 g of talc, 27.0 g of magnesium stearate, 13.5 g of aspartame, 13.5 g of banana flavor, 27.0 g of copolyvidone (Kolliidon VA 64) and 2.625 g of colloidal silicon dioxide, which was admixed in a bag to give mixed powders. This mixed powder was tabletted using a Korsch tablet machine using a round punch having beveled edges with a diameter of 12.7 mm to provide tables weighing 918 mg.

The hardness and disintegration time of each tablet thus obtained was 100-120N and 30-50 seconds respectively.

TABLE 12

Dissolution profile

| Medium → Time (Hour) | 1 | 2 | 3 | Medium → Time (Hour) | 5 |
|---|---|---|---|---|---|
| | % Release | | | | % Release |
| 1 | 48.1 | 43.9 | 4.2 | 0.5 | 33.7 |
| 2 | 60.7 | 58.6 | 4.7 | 1 | 42.9 |
| 4 | 81.1 | 79.2 | 6.4 | 2 | 51.42 |
| 6 | 95.1 | 96.2 | 7.8 | 3 | 55.29 |
| 8 | 102.5 | 106.7 | 18.4 | 5 | 60.5 |
| 10 | 106.1 | | | 7 | 64.4 |
| 12 | | | | 9 | 66.9 |
| 14 | | | | 11 | 71.7 |
| 24 | | | | 13 | 73.5 |
| | | | | 25 | 81.5 |

A pilot, single dose, randomized, 2 period, 2 treatment, 2-way crossover, bioavailability study of controlled release lamotrigine (test formulation) (1×10 mg, as prepared above) versus conventional release lamotrigine (reference formulation) (1×100 mg) tablets in healthy subjects (n=9) under fasting conditions. The peak (Cmax) to end dose (plasma concentration at 24 hours) ratio is given in Table 13.

TABLE 13

| | Peak (Cmax) to End Dose (24 Hr Plasma Concentration) Ratio | |
|---|---|---|
| Volunteer No. | Test Formulation | Reference Formulation |
| 1 | 1.00 | 1.64 |
| 2 | 1.12 | 1.87 |
| 3 | 1.34 | 1.94 |
| 4 | 1.23 | 1.52 |
| 5 | 1.14 | 1.52 |
| 6 | 1.09 | 1.49 |
| 7 | 1.22 | 2.13 |
| 8 | 1.12 | 1.64 |
| 9 | 1.18 | 2.18 |
| Mean | 1.16 | 1.77 |
| S.D. | 0.10 | 0.27 |
| C.V. % | 8.37% | 15.13% |

The ratio of peak to end-dose plasma concentration is close to 1 (mean 1.6±0.1) in majority of the volunteers in the controlled release formulation (test) while it is closer to (mean 1.77±0.27) in majority of the volunteers in the conventional release formulation (reference)

Example 12

1) Production of Core
   Same as prepared in example 11
2) Production of Controlled Release Particles
   Coat I
   A fluidized bed process of wurster type (manufactured by Glatt, Germany), GPCG-3 was charged with 1500 g of above drug granules. A controlled release rate controlling membrane coating liquid of following composition prepared in advance was sprayed. The coated particles were dried in a stream of hot air in tray drier and sifted through 425 µm and 180 µm sieves to provide 1812 g of controlled release particles. The over size and under size controlled release particles were discarded.
   Rate Controlling Coating Membrane Composition

| Eudragit RS 30D | 640.6 g |
|---|---|
| Eudragit RL 30D | 80.45 g |
| Eudragit L 30D 55 | 160.9 g |
| Triethyl citrate | 119.46 g |
| Silicon dioxide (Syloid 244FP R.T.M.) | 70.95 g |
| Purified Water | 600 g |

Coat II
   A Wurster type GPCG-3 coater (manufactured by Glatt, Germany) was charged with 700 g of controlled release particles prepared above (after coat I). A controlled release rate controlling membrane coating liquid of the following composition that was prepared in advance was sprayed. The coated particles were dried in a stream of hot air in tray drier and sifted through 425 µm and 180 µm sieves to provide 714 g of controlled release particles.
   The over size and under size controlled release particles were discarded.
   Rate Controlling Coating Membrane Composition

| Eudragit L 30 D 55 | 129.29 g |
|---|---|
| Triethyl citrate | 11.6 g |
| Glycerol monostearates (GeleolPastiles R.T.M) | 1.92 g |
| Tween 80 | 0.19 g |
| Purified Water | 80.68 g |

3) Production of Dispersible Tablets

To 6.78 of core particles prepared above (without coating of rate controlling membrane) and 26.69 g of controlled release particles prepared above added 85.06 of mannitol (Pearlitol SD 200 R.T.M.), 6.75 g of crospovidone (Polyplasdone XL 10 R.T.M.), 1.35 g of talc,2.7 g of magnesium stearate, 1.35 g of aspartame 1.35 g of banana flavour, 2.7 g of copolyvidone (Kollidon VA 64 R.T.M.) and 0.262 g of colloidal silicon dioxide, which was admixed in a bag to give mixed powders. This mixed powder was tabletted using a Korsch tabletting machine with a round punch having beveled edges, 12.7 mm in diameter to provide tablets each weighing 900 mg.

The hardness and disintegration time of each tablet thus obtained was 100-120 N and 40-60 seconds respectively.

The dissolution rate of tablets was estimated (Table 14).

TABLE 14

Dissolution profile

| Medium → Time (Hour) | 1 % Release | 2 | 3 | Medium → Time (Hour) | 5 % Release |
|---|---|---|---|---|---|
| 1 | 45.0 | 35.1 | 48.1 | 0.5 | 30.5 |
| 2 | 57.7 | 52.5 | 55.3 | 1 | 37.4 |
| 4 | 76.1 | 80.1 | 63.8 | 2 | 56.7 |
| 6 | 89.5 | 90.6 | 71.1 | 3 | 63.7 |
| 8 | 96.0 | 103.3 | 79.2 | 5 | 72.4 |
| 10 | 102.6 | 105.0 | 82.1 | 7 | 81.4 |
| 12 | | | 83.4 | 9 | 83.3 |
| 24 | | | 91.1 | 11 | 88.8 |
| | | | | 13 | 88.5 |
| | | | | 25 | 96.8 |

The invention claimed is:

1. A multiparticulate controlled release dosage formulation of lamotrigine or a pharmaceutically acceptable salt thereof, which comprises:
   (a) core particles, comprising lamotrigine and, said core particles being covered with a release rate controlling polymer selected from the group consisting of poly (ethyl acrylate, methyl methacrylate, trimethylammonioethyl methacrylate chloride) 1:2:0.1; poly(ethyl acrylate, methyl methacrylate, trimethylamonioethyl methacrylate chloride) 1:2:0.2; polymethacrylic acid, ethyl acrylate 1:1; poly(ethyl acrylate, methyl methacrylate) 1:1 or mixtures thereof wherein said release rate controlling polymer includes a plasticizer in the release rate controlling polymer; and (b) a rapidly disintegrating binder on said core particles which allows said core particles to rapidly disperse in an aqueous environment and is further characterized in that when orally administered to a human subject, said core particles will achieve a peak to trough plasma concentration ratio of between 1 to 1.6.

2. The multiparticulate controlled release dosage formulation of lamotrigine as defined in claim 1, wherein the core particles are in the form of a discrete pellet.

3. The multiparticulate controlled release dosage formulation of lamotrigine as defined in claim 1, wherein the core particles are homogenous.

4. The multiparticulate controlled release dosage formulation of lamotrigine as defined in claim 1, wherein the core particles are heterogenous.

5. The multiparticulate controlled release dosage formulation of lamotrigine as defined in claim 1, wherein the formulation is in the form of tablet.

6. The multiparticulate controlled release dosage formulation of lamotrigine as defined in claim 1, which comprises a once a day dosage formulation.

7. The multiparticulate controlled release dosage formulation of lamotrigine as defined in claim 1, wherein the core comprises an organic acid.

8. The multiparticulate controlled release dosage formulation of lamotrigine as defined in claim 1, wherein the rate controlling polymer is coated with an enteric coating.

9. The controlled release formulation of lamotrigine for oral administration as defined in claim 1, wherein the core comprises a blend of different types of controlled release particles of lamotrigine having different release profiles.

10. The multiparticulate controlled release dosage formulation of lamotrigine as defined in claim 1 or 9, wherein the particles have the following release profile when measured in a U.S.P.XXII Type II (paddle) apparatus at a temperature of 37° C. at 50rpm using a 0.1M HCl medium for 1 hour and thereafter a trisodium phosphate buffer at pH 6.8 for the remaining hours:
   a) not more than 60% of the total lamotrigine is released in 1 hour;
   b) not less than 35% of the total lamotrigine is released after 6 hours of measurement;
   c) not less than 60% of the total lamotrigine is released after 25 hours of measurement.

11. The multiparticulate controlled release dosage formulation of lamotrigine as defined in claim 1 or 9, wherein the particles have the following release profile when measured in a U.S.P.XXII Type II (paddle) apparatus at a temperature of 37° C. at 50 rpm using a pH 4.5 buffer:
   a) not more than 60% of the total lamotrigine is released in 1 hour;
   b) not less than 35% of the total lamotrigine is released after 6 hours of measurement;
   c) not less than 60% of the total lamotrigine is released after 24 hours of measurement.

12. The multiparticulate controlled release dosage formulation of lamotrigine as defined in claim 1 or 9, wherein the particles have the following release profile when measured in a U.S.P.XXII Type II (paddle) apparatus at a temperature of 37° C. at 50 rpm in 0.1 M HCl:
   a) not more than 60% of the total lamotrigine is released in 1 hour;
   b) not less than 35% of the total lamotrigine is released after 6 hours of measurement;
   c) not less than 60% of the total lamotrigine is released after 24 hours of measurement.

13. The multiparticulate controlled release dosage formulation of lamotrigine as defined in claim 1 or 9, wherein the particles have the release profile, when measured in a U.S.P.XXII Type II (paddle) apparatus at a temperature of 37° C. at 50 rpm at pH 7.5, not more than 60% of the total lamotrigine is released in 1 hour.

14. The multiparticulate controlled release dosage formulation of lamotrigine as defined in claim 1 or 9, wherein the particles have the release profile, when measured in a U.S.P.XXII Type II (paddle) apparatus at a temperature of 37° C. at 50 rpm at a pH of 6.8, not more than 60% of the total lamotrigine is released in 1 hour.

15. The controlled release formulation of lamotrigine for oral administration as defined in claim 1 in admixture with free lamotrigine or a pharmaceutically acceptable salt thereof.

16. A method for reducing fluctuation in the troughs and peaks of drug concentration in patient's blood plasma, which comprise administering orally to a patient in need thereof a controlled release formulation of Lamotrigine as defined in claim 1.

17. A method for improving the patient's compliance with Lamotrigine therapy by reducing the frequency of dosing to once daily, said method comprising administering orally to a patient in need thereof a controlled release formulation containing Lamotrigine as defined in claim 1.

18. A method for the safer administration of Lamotrigine while in combination with drugs selected from the group consisting of phenytoin, carbamazepine, sodium valproate, which comprises administering orally to a patient in need thereof a controlled release formulation containing Lamotrigine as defined in claim 1.

19. A method for providing therapeutic blood plasma concentration of Lamotrigine over a 24 hours period with diminished incidence of ataxia, diplopia, somnolence, headache and rash, which comprises administering orally to a patient in need thereof a controlled release formulation containing Lamotrigine as defined in claim 1.

20. The multiparticulate controlled release dosage formulation of lamotrigine as defined in claim 1, wherein the rate controlling polymer is poly(ethyl acrylate, methyl methacrylate) 1:1 and the plasticizer is triethyl citrate.

* * * * *